United States Patent [19]

Dean et al.

[11] Patent Number: 5,162,505

[45] Date of Patent: * Nov. 10, 1992

[54] PROTEINS MODIFIED WITH POSITIVELY CHARGED CARRIERS AND COMPOSITIONS PREPARED THEREFROM

[75] Inventors: Richard T. Dean, Downingtown, Pa.; Raymond H. Boutin, Wilmington, Del.; John Lister-James, Glenmoore, Pa.

[73] Assignee: Centocor, Malvern, Pa.

[ * ] Notice: The portion of the term of this patent subsequent to Sep. 1, 2009 has been disclaimed.

[21] Appl. No.: 409,150

[22] Filed: Sep. 19, 1989

[51] Int. Cl.$^5$ .................. C07K 17/06; C07K 15/28; A61K 49/02

[52] U.S. Cl. .................. 530/391.5; 530/331; 530/391.3; 530/408; 530/409; 424/85.91; 424/1.1; 514/21; 525/54.1

[58] Field of Search .............. 530/331, 388, 408, 409, 530/391.5, 391.3; 525/54.1; 514/21; 424/85.91, 1.1

[56] References Cited

U.S. PATENT DOCUMENTS

| | | | |
|---|---|---|---|
| 4,659,839 | 4/1987 | Nicolotti et al. | 548/546 |
| 4,671,958 | 6/1987 | Rodwell et al. | 424/85.91 |
| 4,897,255 | 1/1990 | Fritzberg et al. | 424/1.1 |
| 4,943,636 | 7/1990 | Niteck et al. | 546/294 |
| 4,994,385 | 2/1991 | Bieniarz et al. | 435/177 |

FOREIGN PATENT DOCUMENTS

| | | |
|---|---|---|
| 1079268 | 6/1980 | Canada . |
| 173629 | 3/1986 | European Pat. Off. . |
| 188256 | 7/1986 | European Pat. Off. . |
| 79/00515 | 8/1979 | World Int. Prop. O. . |

OTHER PUBLICATIONS

Hashida et al (1984) J. Applied Biochem 6:56.
Srinivasachar et al (1989) Biochemistry 28(6):2501-2509.
Yoshitake et al (1979) Eur. J. Biochem. 101:395-399.
I. Pastan, M. C., Willingham and D. J. P. Fitzgerard, Cell, 47, 641-48 1986.
Childs, R. L., and Hnatowich, D. J., J. Nucl. Med., 26, 293-299, 1985.
B. A. Khaw, et al., J. Nucl. Med., 27, 909-10, 1986, Abstract No. 137.
Y. Manabe, C. Longley and P. Furmanski, Biochem. Biophys. Acta, 883, 460-67 (1986).
V. P. Torchilin, et al., Hybridoma, 6, 229-40, 1987.
B. M. Brenner, T. H. Hostetter and H. D. Humes, Am. J. Physiol., 234, F455-60, 1987.
A. Steinstrasser, et al., J. Nucl. Med., 28, 693, 1987, Abstract No. 575.
D. A. Goodwin, J. Nucl. Med., 28, 1358-62, 1987.
Khaw, et al., Biochem. Biophys. Res. Comm., 209, 295-97 (1980).
Krajcarek, et al., Biochem. Biophys. Res. Comm., 77, 581-85 (1977).
Eary, J. et al., J. Nucl. Med., 28, 650-51 (1987), Abstract No. 391.
A. R. Fritzberg, et al. Proc. Nat. Acad. Sci. USA, 85 4025-29 (1988).
T. Z. Coimbra, M. R. Furtado, J. J. Lachat, and I. F. de Carvalho, Nephrom, 33, 208-15, 1983.

Primary Examiner—Christine M. Nucker
Assistant Examiner—Kay K. Kim
Attorney, Agent, or Firm—Woodcock, Washburn, Kurtz, Mackiewicz & Norris

[57] ABSTRACT

Protein conjugates comprising a protein covalently linked to at least one positively charged agent, so that the protein conjugate has an overall net positive charge in aqueous conditions at physiological pH are disclosed. The positively charged agents comprise polymers of three or more subunits selected from the group consisting of amino acids containing positively charged side chains and alkylamines. These protein conjugates have decreased blood clearance rates compared to conjugates which do not have the positively charged agents. The protein conjugates may further comprise diagnostic or therapeutic radionuclides bound to the protein or the positively charged agent through bifunctional coupling agents.

46 Claims, No Drawings

PROTEINS MODIFIED WITH POSITIVELY CHARGED CARRIERS AND COMPOSITIONS PREPARED THEREFROM

FIELD OF THE INVENTION

This invention relates to the field of target-specific proteins and, more particularly, to immunodiagnostics and immunotherapy.

BACKGROUND OF THE INVENTION

Certain proteins, when introduced into an organism, have been shown to specifically localize to and bind to target sites. These target-specific proteins can be used as carriers of diagnostic and therapeutic agents, allowing such agents a means of specifically localizing to the target. The use of target-specific proteins as carriers involves the binding of the diagnostic or therapeutic agent to the protein; forming a conjugate which combines the diagnostic or therapeutic properties as well as the localization properties of the protein.

The use of monoclonal antibodies and antibody fragments as target-specific carriers of diagnostic or therapeutic agents should ideally provide an efficient means of localizing such agents to target tissue. Monoclonal antibodies are highly specific and can be used, for example, for imaging specific target sites or as vehicles to deliver substances to target sites. In recent years numerous monoclonal antibodies have been developed with affinity for targets such as atherosclerotic tissue, fibrinogen, myosin and tumors, to name just a few, and work in this area continues. The attachment of radiometals to proteins, especially antibodies and antibody fragments, results in the formation of new radiodiagnostic and radiotherapeutic agents. The performance of the radiometal-protein conjugates depends on a number of factors, such as the stability of the radiometal-protein bond and the ability of the conjugates to localize to the target tissue.

Proteins and antibodies have been shown to form stable bonds to radiometals by the use of bifunctional coupling agents. The bifunctional agent is selected such that it is capable of binding radiometals by chelation and also form a stable linkage to the protein. Thus, the protein or antibody is bound to the radiometal through the bifunctional coupling agent. For example, diethylenetriaminepentaacetic acid (DTPA) has been conjugated onto an antimyosin antibody, and the protein-bound DTPA used to chelate indium-111 (Khaw, et al., *Science*, 209, 295-97 (1980). See also Krejcare, et al., *Biochem. Biophys. Res. Comm.*, 77, 581-85 (1977) and Childs, R. L. and Hnatowich, D. J., *J. Nucl. Med.*, 26, 293 (1985)). This approach has also been used where particular diaminodithiol and diamidedithiol chelating agents have been coupled to antibodies (Fritzberg, et al., *J. Nucl. Med.*, 27, 957-58 (1986), Eary, J. et al., *J. Nucl. Med.*, 28, 650-51 (1987) and A. R. Fritzberg, et al., *Proc. Nat. Acad. Sci. USA*, 85, 4025-29 (1988)). Chelated radiometals and bifunctional coupling agents have been linked to proteins by lysyl side chain amino groups (EPO Publication No. 188, 256). Chelators have also been site selectively attached to oxidized antibody carbohydrate moieties (EPO Publication No. 173, 629, U.S. Pat. No. 4,671,958). Chelators can also be attached by reaction with free sulfhydryl groups (U.S. Pat. No. 4,659,839, U.S. Pat. No. 4,671,958 and EPO Publication No. 173, 629).

Useful thiol-containing bifunctional agents for the attachment of radionuclides to proteins have been disclosed (pending U.S. Ser. No. 199,931, filed Jun. 15, 1988 and pending U.S. Ser. No. 235,999, filed Aug. 24, 1988). These disclosures demonstrate the usefulness of sulfhydryl-selective attachment of bifunctional agents to protein sulfhydryls and the subsequent removal of thiol protecting groups from the chelating portion of the bifunctional agents. Also demonstrated was a reduction of radionuclide accumulation in the excretory organs by the use of cleavable linking moieties. These cleavable linking moieties are used to join the chelating portion and the sulfhydryl-selective portion of the bifunctional agents.

Antibodies and antibody fragments have also been used as target specific carriers of toxins and drugs for therapeutic purposes. For example, the polypeptide toxin Ricin consists of two peptide chains. The A chain is toxic to cells, and can be covalently linked to antibodies or antibody fragments and specifically delivered to target cells (I. Pastan, M. C. Willingham and D. J. P. Fitzgerald, *Cell*, 47, 641-48 (1986)). Antibodies have also been used as specific targeting carriers of a variety of antineoplastic agents (D. C. Edwards, *Pharmac. Ther.*, 23, 147-77 (1983)).

The utility of a target-specific protein conjugate can be enhanced by the addition of increasing amounts of an agent to the protein. For example, the addition of multiple chelating sites allows greater specific activities per protein molecule by binding larger numbers of radionuclides. Antibodies and antibody fragments have been shown to be sensitive to the number of chelators directly bound to them (Childs, R. L. and Hnatowich, D. J., *J. Nucl. Ned.*, 26, 293 (1985)). Multiple chelating sites have been attached to a single site on an antibody by the use of a carrier (B. A. Khaw, et al., *J. Nucl. Med.*, 27, 909-10 (1986); Y. Manabe, C. Longley and P. Furmanski, *Biochim. Biophys. Acta*, 883, 460-67 (1986); V. P. Torchilin, et al., *Hybridoma*. 6, 229-40 (1987)). This approach involves the attachment of many diethylenetriaminepentaacetic acid moieties to poly-lysine, resulting in a net negative charge of the poly-lysine carrier. The antibodies and antibody fragments so modified were observed to localize in the liver, with an increase in blood clearance rates.

Clearance of small proteins from the blood in vivo occurs largely in the kidneys. Movement across the glomerular capillary barrier is dependant on both size and the charge of the protein (B. M. Brenner, T. H. Hostetter and H. D. Humes, *Am. J. Physiol.*, 234, F455-60 (1987)). Increasing the positive charge (increasing pI) is known to facilitate glomerular filtration. However, a study of cationically modified autologous albumin found that a decreased accumulation in the urine occurred (T. Z. Coimbra, M. R. Furtado, J. J. Lachat and I. F. de Carvalho, *Nephron*, 33, 208-15 (1983)).

Means have been found for preparing stable protein-radiometal conjugates which localize to target tissue. The distribution characteristics in vivo of the protein-radiometal conjugates have not been modified in a controllable fashion. For example, the in vivo tumor to blood ratio of a specific monoclonal antibody was lower for iodination (I-131), but independent of labeling using Tc-99m, Se-75 and In-111 (A. Steinstrasser, et al., *J. Nucl. Med.*, 28, 693 (1987)). D. A. Goodwin states (*J. Nucl. Med.*, 28, 1358-62 (1987)) that although antibody fragments (Fab and F(ab')$_2$) are able to diffuse more rapidly into tumors than whole antibodies, absolute tumor concentrations will be lower for the fragments relative to the whole antibody due to lower integral blood concentrations. From this, the conclusion can be drawn that a more effective radioimmunotherapeutic agent would need the diffusion characteristics of an antibody fragment, yet would also need an increased blood residence time to achieve greater tumor accumulation.

SUMMARY OF THE INVENTION

It has now been found that the blood clearance rate of protein conjugates can be decreased in vivo by the attachment of positively charged agents to the protein so that the conjugate itself has a net positive charge. This invention therefore relates to a protein conjugate comprising a protein covalently linked to at least one positively charged agent, said protein conjugate having a net positive charge in aqueous solution at physiological pH (about 7.0–7.5), and said positively charged agent comprising a polymer of three or more subunits selected from the group consisting of amino acids containing positively charged side chains and alkylamines. The protein may itself have a pharmaceutical use, e.g., as a diagnostic or therapeutic agent, or may be used as a carrier of diagnostic or therapeutic agents. The diagnostic or therapeutic agents may be bound to either the protein or to the positively charged agent, preferably through a bifunctional coupling agent.

This invention further relates to a radiodiagnostic or radiotherapeutic precursor having a net positive charge in aqueous solution at physiological pH and comprising an antibody or antibody fragment having the above positively charged agent bound to the antibody or antibody fragment and one or more bifunctional coupling agents bound to either the antibody or antibody fragment, or bound to the positively charged agent. Addition of a suitable radionuclide to the precursor results in binding of the radionuclide by the coupling agent(s) and formation of a radiodiagnostic or radiotherapeutic agent. The invention therefore still further relates to a radiodiagnostic or radiotherapeutic agent having a net positive charge in aqueous solution at physiological pH and comprising an assembly of an antibody or antibody fragment, a positively charged agent bound thereto, one or more bifunctional coupling agents bound either to the antibody or antibody fragment or to the positively charged agent, and a suitable radionuclide bound to said bifunctional coupling agents.

The protein conjugates of this invention are advantageous for a number of reasons. One advantage is that the blood concentration of a radionuclide-protein conjugate can be increased in vivo. This increase in concentration is not accompanied by a significant increase in molecular weight, so that the enhanced diffusion characteristics of a Fab' fragment relative to a IgG is retained. Another advantage of the method is that the positively charged agent can be used as a carrier of more than one therapeutic or diagnostic agents to a single site on the protein, allowing the biological effect of the protein conjugate to be increased by binding increased amounts of the therapeutic or diagnostic agents per protein molecule without impairing biological activity.

DETAILED DESCRIPTION OF THE INVENTION

The invention relates to a method for decreasing the blood clearance rate of proteins in vivo, without substantially increasing the molecular size, by attachment of positively charged agents to the protein so that the resulting protein has a net positive charge in aqueous solution at physiological pH. The net charge of a protein conjugate can be measured by methods known in the art such as isoelectric focusing or by the use of ion exchange media. The term "protein conjugate" as used herein is intended to include a conjugate of a pharmaceutical protein and at least one positively charged agent bound thereto. The pharmaceutical protein may itself be useful as a therapeutic or diagnostic agent or may serve as a carrier for such agents, e.g., radionuclides.

Suitable positively charged agents are molecules which maintain a net positive charge in aqueous solution at physiological pH. Positively charged agents useful in the invention are polymers of three or more subunits selected from the group consisting of amino acids containing positively charged side chains and alkylamines. The term "polymer" is used herein to broadly encompass both polymers and copolymers. Positively charged side chains included alkylamines, alkylamidines and alkylguanidines, each optionally substituted with one or more alkyl groups. Specific examples of positively charged agents include polymers and copolymers of amino acids such as lysine, ornithine, 2,4-diaminobutyric acid, and arginine, and the polymer polyethylenimine. Preferred for use in the invention are well defined polymers consisting of 3–10 repeat units of the monomer. Most preferred are L-lysine polymers of 4–8 lysines, said lysines linked together as amides via the alpha amine and the carboxylate.

The positively charged agent is bound to a protein by a stable covalent linkage. Said linkage can be effected directly to the protein by methods well known to those skilled in the art. For example, the protein can be treated with an excess of the positively charged agent and a limiting amount of a water soluble carbodiimide (e g. 1-3-dimethylaminopropyl-3-ethylcarbodiimide), or other agent known to form amide bonds in aqueous solution.

Preferably, however, the positively charged agent is linked indirectly to the protein through a bonding radical capable of covalently bonding to a site on the protein and also capable of bonding to a site on the positively charged agent. The bonding radical suitable for linking the positively charged agent to the protein may comprise a compound of the formula E—L—A where E is a moiety capable of covalently bonding to a site on the protein, A is a moiety capable of covalently bonding to a site on the positively charged agent, and L is a linking agent.

Methods of bonding the bonding radical to the positively charged agent through moiety A are well known to those skilled in the art. Examples of such moieties A which would be capable of bonding with a site on an amino acid polymer or copolymer or on polyethyleneimine include active esters, imidate esters and epoxides. Preferably, the moiety is an active ester, the term active ester" referring to an ester of a carboxylic acid which reacts with amines to form amide bonds at an appreciable rate in aqueous solution. The most preferred active ester is an ester of N-hydroxysuccinimide. An example of a suitable imidate ester is methyl imidate, and examples of suitable epoxides are amides of 2,3-epoxy propylamine. Reductive alkylation using aldehydes, e.g., glycinal amides, may also be used to bond the positively charged agent in which suitable moieties A would include aldehydes. Amino groups on the positively charged agent form imines by reaction with aldehydes, and this linkage can then be stabilized by reduction to an amine using suitable reducing agents, for example, sodium cyanoborohydride.

In the above-mentioned formula, E is a function capable of reacting with a site on the protein. E may be a sulfhydryl selective electrophile, including those in the group of haloalkyl, sulfonate ester, maleimide and aziridine. Preferably, the sulfhydryl electrophile is selected from the group consisting of $ClCH_2CONH-$, $BrCH_2CONH-$, $ICH_2CONH-$ and N-substituted maleimide, the most preferred sulfhydryl electrophile being maleimide. E may also be an amine or hydrazine derivative capable of reacting with protein carboxyls or oxidized carbohydrate. In addition, E may be a group which can react with antibody amino groups such as the active esters, imidate esters, epoxides and aldehydes mentioned above as suitable moieties A.

L is a linking radical having at least two valencies for joining the electrophile E and the positively charged agent-reactive moiety A. Preferred organic linking radicals are selected from the group consisting of optionally substituted alkyl, optionally substituted alkyl containing heteroatom substituents for carbon (e.g., in which a carbon in the aliphatic chain is replaced with a heteroatom such as N, O or S), and optionally substituted aryl groups. The term "alkyl" as used herein includes branched, cyclic and straight-chain alkyl groups. The term "optionally substituted" as used herein refers to optional substitution with functional groups, such as but not limited to, alkoxy groups, alkyl groups, aryl groups, hydroxy groups and carboxy groups, which will not interfere with the desired coupling and labeling reactions. Generally speaking, such functional groups are unreactive to reaction with mercaptans, sulfides, amines, acylating and alkylating agents. Examples of preferred linking radicals are $-CH_2cyclo-C_6H_{10}-$, $-CONHCH_2CH_2-$, $-CH_2C_6H_4-$, $-NHCH_2CH_2-$ and $-OCH_2CH_2OCH_2CH_2OCH_2CO$.

An example of a bonding radical useful for covalently bonding a positively charged agent to a protein according to this invention is the compound 3-sulfosuccinimidyl 4-(N-maleimido methyl)cyclohexane-1-carboxylate, compound I.

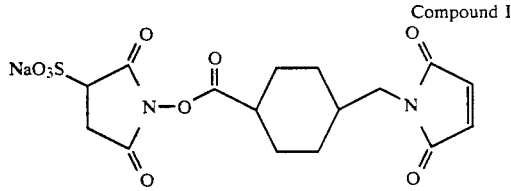

Compound I

The invention is useful for the modification of protein molecules. One of the preferred embodiments of the invention is to prepare immunodiagnostic and immunotherapeutic agents from antibody fragments. Antibody fragments can be prepared from antibodies by treatment with proteolytic agents. Preferred antibody fragments are F(ab')$_2$, Fab, Fab' and Fv. Most preferred is the Fab' fragment which contains free sulfhydryl groups when maintained under non-oxidizing conditions. The Fab' fragment can be prepared from antibodies by treatment with a proteolytic agent (such as pepsin) to produce the F(ab')$_2$ fragment containing two antigen binding sites. Reduction of the F(ab')$_2$ fragment with suitable reducing agents, such as dithiothreitol, generates the monovalent Fab' containing free sulfhydryls. As these sulfhydryls are located distally to the antigen binding portion of the Fab' fragment they provide a preferred site for selective attachment of the positively charged agent without impairing antigen binding.

The positively charged agent can be used as a carrier of multiple chelating, diagnostic or therapeutic agents while also decreasing the blood clearance rates of proteins. Although the diagnostic or therapeutic agents may be bonded directly to the protein, bonding them to the positively charged agent allows an increase in the number of chelating sites or the number of diagnostic or therapeutic agents available per protein molecule without increasing the number of modification sites on the protein. For example, a suitable poly-L-lysine can be reacted at several epsilon amino groups with diagnostic, chelating or therapeutic agents to produce a positively charged agent carrying a controlled number of such agents. This process can be controlled by manipulation of the relative and absolute concentrations of the positively charged agent and the chelating, diagnostic or therapeutic agent. Optimal conditions can be determined by one skilled in the art. The modified positively charged agent carrying the multiple agents can then be site-selectively attached to proteins using suitable reagents as described above. Chelating, diagnostic and therapeutic agents containing functional groups that are negatively charged at physiological pH values, for example diethylenetriaminepentaacetic acid, can also be used in the invention. However, the number of remaining positive charges on the positively charged agent must exceed the number of negative charges added together with the number of positive charges neutralized by modification. That is, the number of negative charges added and the number of positively charged sites should be adjusted such that the resultant product have a suitable net positive charge. Most preferably the net positive charge should be between 2 and 6 inclusive.

Diagnostic or therapeutic radionuclides such as Tc, In, Ga, Re, I and Y may be complexed with the protein conjugate, either to the protein or to the positively charged agent, through bifunctional coupling agents capable of chelating the radionuclide. Preferred bifunctional coupling agents are of the form E'—L'—Ch wherein E' is a group capable of forming a stable bond to either the protein or to the positively charged agent, L' is a linking radical and Ch is a radionuclide chelator.

The group capable of forming a stable bond to either the protein or to the positively charged agent, E', may be a sulfhydryl selective electrophile as described above, an amine or hydrazine derivative capable of reacting with protein carboxyls or oxidized carbohydrate or a group which can react with antibody amino groups as described above in connection with the moiety A, such as active esters, imidate esters, epoxides and aldehydes.

The chelator, Ch, is that portion of the bifunctional coupling agent which forms a bond with the radionuclide. The chelator can be selected from those chelators known to bind the radionuclide of interest with sufficient stability to be used in vivo. Attachment of the chelator to the binding radical L' and the electrophilic group E' can be attained by one skilled in the art. In one embodiment of the invention the chelating moiety preferably contains at least one protected thio group. The thiol-containing chelating moiety is suitably protected from reaction with electrophilic moieties during attachment of the positively charged agent to the protein or positively charged agent. As used herein, the expression "protected thiol" refers to a thiol-containing moiety wherein the thiol group(s) is (are) reversibly derivatized such that the thiol(s) is(are) rendered unreactive. After attachment to the protein substrate the chelating moiety can be deprotected to unmask the chelating functionality for radionuclide binding.

Groups suitable for protecting the thiol from reaction are organic and inorganic groups which can be readily removed under mild conditions to regenerate the free thiol in the presence of the protein without substantially altering the activity of the protein. In preferred embodiment of the invention, the thiol protecting group is selected from the group consisting of thiol esters, disulfides and Michael-addition products. More preferably the protecting group is a thiol ester.

Preferably the chelator is selected from those of the formulas:

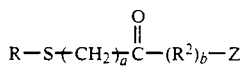

and

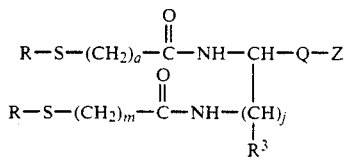

wherein a, j and m are independently an integer of 1 to 3 inclusive, and most preferably 1; b is an integer from 3 to 6, inclusive, and most preferably 3; R is $R^1CO-$ or $R^1S-$ where $R^1$ is methyl, optionally substituted lower alkyl and optionally substituted aryl, and most preferably R is $R^1CO-$ wherein $R^1$ is phenyl or phenyl substituted with a functional group; each $R^2$ is independently selected from the units

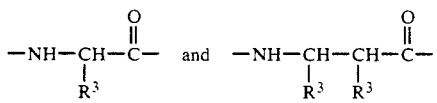

and most preferably $R^2$ is $NHCH(R^3)CO-$ where each $R^3$ is independently selected from hydrogen, optionally substituted lower alkyl, optionally substituted aryl, and most preferably $R^3$ is hydrogen; Q is a carbonyl group or $-CHR^3-$; and Z designates the site of attachment of the organic linking radical L'. The term "alkyl" as used herein includes branched and straight chain alkyl groups, and "lower alkyl" refers to such groups having up to six carbon atoms. The term "optionally substituted" as used herein refers to optional substitution with functional groups, such as but not limited to alkoxy groups, alkyl groups, aryl groups, hydroxy groups and carboxy groups, which will not interfere with the desired coupling and labeling reactions. Generally speaking, such functional groups are unreactive to reaction with mercaptans, sulfides, amines, acylating and alkylating agents.

The organic linking radical, L', has at least two valencies for joining the electrophilic moiety E' and the chelating moiety Ch. Suitable linking radicals include those described above in connection with definition of the moiety L. In addition, the organic linking radical L' may preferably contain one or more cleavable sites, thus enhancing clearance of the radiometal from non-target tissue. In the case of the organic linking radical L', the expression "cleavable site" refers to a chemical bond in the linking radical, the breaking of which bond serves to dissociate the radiometal in chelated form from the protein. Such dissociation should preferably occur at a rate of at least about 50% within the half-life of the radiometal. Most preferably, the cleavable site is an alkyl ester, an ester of an aryl alcohol or an aryl ester of an alkyl alcohol. Preferred linking radicals L' containing cleavable sites are selected from those of the formula:

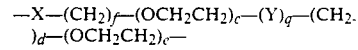

wherein f is an integer from 0 to 6, preferably 2; d and e are independently integers from 0 to 5 inclusive, and preferably 2; c is an integer of from 0 to 5 inclusive, and preferably 1; q is 0 or 1; X is selected from the group consisting of $-NH-$, $-O-$ or S, and preferably $-O-$; Y is selected from the group consisting of $-CH_2COO-$, $-OOCCH_2-$, $-CH_2CONH-$, $-OCH_2COO-$, $-NHCOCH_2-$, and $-OOCCH_2O-$ and is preferably $-OCH_2COO-$; provided that, when X is other than $-O-$, then q is 1 and Y is other than $-CH_2CONH-$ or $-NHCOCH_2-$, and that when f is 0, then c and q are also 0.

Bifunctional coupling agents which may be used in this invention are described in more detail in the following pending patent applications, the disclosures of which are hereby incorporated by reference: U.S. Ser. No. 207,261, filed Jun. 15, 1988; U.S. Ser. No. 235,999, filed Aug. 24, 1988; U.S. Ser. No. 292,502, filed Dec. 30, 1988 now abandoned, and U.S. Ser. No. 312,767, filed Feb. 17, 1989 now U.S. Pat. No. 5,053,50

Specifically preferred bifunctional coupling agents of the invention are those of the formulae:

Compound II

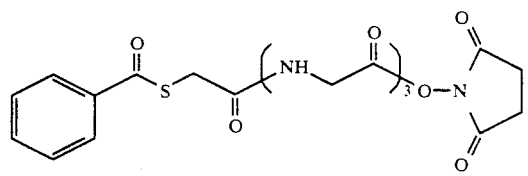

and

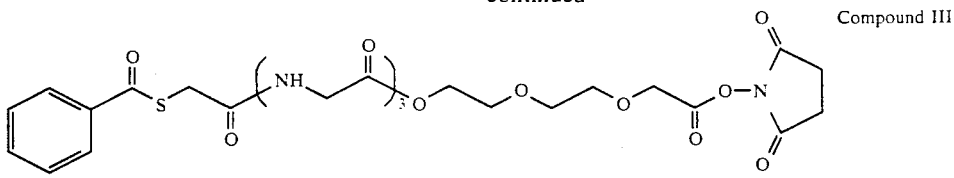

Compound II can be prepared by the following reaction scheme:

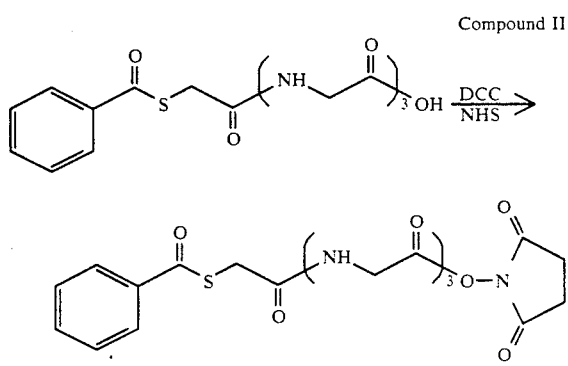

Compound III can be prepared by the following reaction scheme:

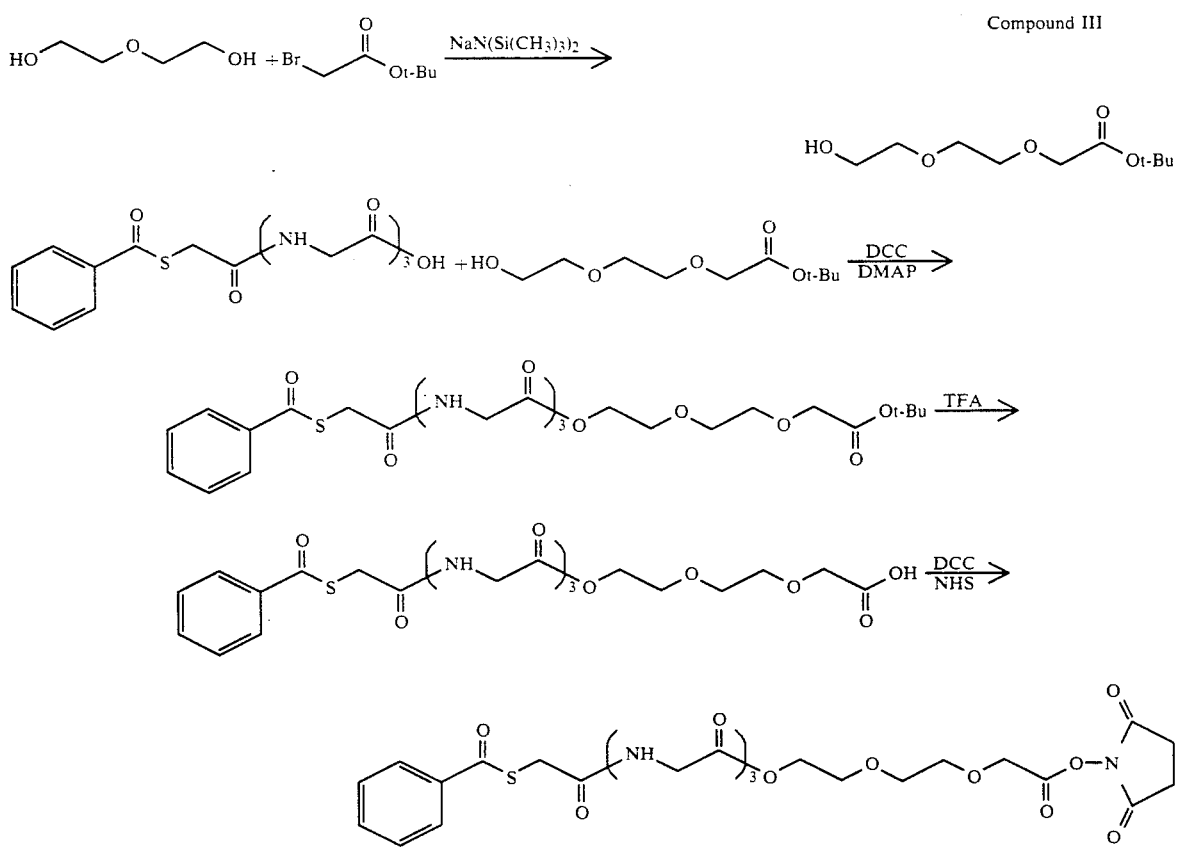

Agents other than bifunctional coupling agents capable of chelating radionuclides can be used to bind radionuclides to the protein conjugates of the present invention. Agents capable of binding non-metallic radionuclides such as iodide isotopes can be reacted with the positively charged agent. The positively charged agent so modified can then be radiolabeled, followed by conjugation with the protein. For example, an activated aromatic ring capable of selectively reacting with radioactive iodide under oxidizing conditions can be attached to the positively charged agent. The positively charged agent modified in this fashion can then be reacted with a suitable iodide isotope and a suitable oxidizing agent. The iodinated positively charged agent can then be coupled to the protein as described above.

Other agents which are known to be toxic or therapeutic by and of themselves can be attached to the positively charged agent. Methods to accomplish this should be apparent to one skilled in the art.

Tables 1 and 2 provide mouse biodistribution data which illustrate the effect of a positively charged agent attached to an antibody Fab' fragment. Table I gives the data for the technetium-99 m labeled conjugate of Compound II and an anti-fibrin Fab' modified with pentalysine. Table 2 gives the data for the technetium-99m labeled conjugate of Compound IV and an anti-fibrin Fab'. The data in Table 2 is from pending U.S. Ser. No. 235,999, filed Aug. 24, 1988.

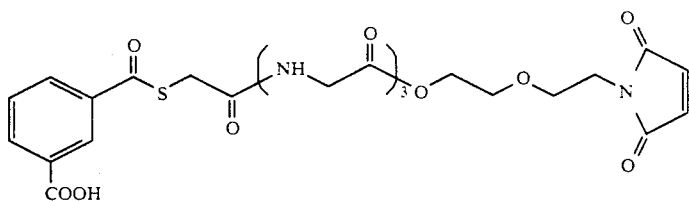

Compound IV

TABLE I

Biodistribution of Technetium-99 m Labeled Fab'-penta-lysine-(2-thioacetyl)glycylglycylglycine Conjugate in Mice
% dose/gram (±sd)

| Organ | Time (h) | | | |
|---|---|---|---|---|
| | 0.5 | 2 | 5 | 24 |
| blood | 29.6 (0.9) | 19.3 (3.7) | 9.88 (1.1) | 1.2 (0.8) |
| heart | 6.5 (1.3) | 4.6 (0.7) | 2.6 (0.2) | 0.5 (0.1) |
| lungs | 7.0 (0.8) | 5.2 (0.7) | 3.2 (0.6) | 0.8 (0.1) |
| liver | 7.7 (0.6) | 6.7 (1.0) | 4.6 (0.5) | 2.0 (0.1) |
| spleen | 4.9 (0.6) | 3.5 (0.7) | 2.0 (0.2) | 0.7 (0.1) |
| kidneys | 28.4 (3.8) | 31.3 (7.6) | 21.0 (2.7) | 11.7 (2.1) |
| stomach | 1.0 (0.3) | 1.5 (0.4) | 2.5 (1.4) | 3.2 (1.9) |
| S.I. | 3.7 (0.3) | 6.7 (1.8) | 3.9 (0.6) | 1.4 (0.6) |
| L.I. | 0.8 (0.0) | 4.4 (2.3) | 10.8 (1.6) | 4.6 (2.3) |
| muscle | 1.0 (0.0) | 0.8 (0.0) | 0.7 (0.1) | 0.2 (0.1) |

TABLE 2

Mouse Biodistribution of Tc-99 m Labeled Antifibrin-Compound IV Conjugate
% dose/gram

| Organ | Time (hrs.) | | | | |
|---|---|---|---|---|---|
| | 0.5 | 1.0 | 2.5 | 5.0 | 24.0 |
| Blood | 14.78 | 10.95 | 4.35 | 1.81 | 0.35 |
| Heart | 2.80 | 2.72 | 1.17 | 0.44 | 0.13 |
| Lungs | 4.68 | 4.51 | 1.67 | 0.94 | 0.26 |
| Liver | 3.78 | 3.36 | 1.93 | 1.20 | 0.76 |
| Spleen | 1.85 | 1.66 | 0.84 | 0.46 | 0.23 |
| Kidneys | 27.31 | 20.99 | 12.19 | 6.81 | 2.72 |
| Stomach | 1.41 | 0.92 | 0.50 | 0.89 | 0.38 |
| S.I. | 2.46 | 3.16 | 3.28 | 1.79 | 0.30 |
| L.I. | 0.64 | 0.53 | 4.53 | 4.34 | 1.09 |
| Muscle | 0.53 | 0.45 | 0.39 | 0.28 | 0.05 |

EXAMPLES

The invention is further described in the following examples. All temperatures are degrees Celsius. NMR spectra are given for $^1$H at 300 MHz using TMS as an internal standard.

Example I: Preparation of succinimidyl (2-benzoylthioacetyl)glycylglycylglycinate (Compound II)

a) Preparation of (2-benzoylthioacetyl)glycylglycylglycinate

To a rapidly stirred mixture of water (170 mL), tetrahydrofuran (90 mL), sodium bicarbonate (8.44 g. 0. 10 mol) and glycylglycylglycine (3.80 g, 0.02 mol) was added 5.89 g of succinimidyl 2-benzoylthioacetate (R. F. Schneider, et al., J. Nucl. Med., 25, 223-29 (1984)). The mixture was stirred at room temperature for one hour. The tetrahydrofuran was removed by rotary evaporator (water aspirator, 30.). The resultant solution was diluted to 300 mL with water, and concentrated hydrochloric acid added to give a pH of 2-3. The product became a white precipitate during acidification. The product was collected by filtration. The white precipitate was dissolved in 120 mL of hot acetone with 20 mL of water added. The cloudy solution was filtered while hot, heated to boiling and 150 mL of water added slowly while heating. The solution was allowed to cool slowly to room temperature, during which time a white solid formed. The solution was allowed to stand at 4° overnight, and the product was collected by filtration. The product was then dried over $P_2O_5$ under vacuum for 48 hours. obtained 4.44 g (60%) of material. NMR matched that previously reported (A. R. Fritzberg, et al., J. Nucl. Med., 27, 111–16 (1986)).

b) Preparation of succinimidyl (2-benzoylthioacetyl)glycylglycylglycinate

To a solution of 1.0 g of (2-benzoylthioacetyl)glycylglycylglycine (2.72 mmol) in 10 mL of dimethylforamide was added 0.56 g of dicyclohexylcarbodiimide (2.72 mmol) and 0.31 g of N-hydroxysuccinimide (2.72 mmol). The solution was stirred at room temperature for 24 hours. The resultant white solid was filtered off. The solvent was removed from the filtrate by rotary evaporator (vacuum pump, 35.) to give the product as a yellow semisolid. This solid was dried under vacuum overnight. The product was then recrystallized from 100 mL of hot 2-propanol to give 0.27 g of a white powder after filtration and drying under vacuum (21%). NMR (DMSO-$d_6$)δ 2.81 (s, 4H), 3.79 (m, integral obscured by water), 3.89 (s, integral obscured by water), 4.28 (d, 2H), 7.58 (d, 2H), 7.71 (t, 1H), 7.93 (d,2H), 8.29 (br t, 1H), 8.54 (m, 2H).

Example II. Preparation of succinimidyl 8-carboxy-3,6-dioxaoctyl-2-benzoylthioacetyl)glycylglycylglycinate (Compound III).

a) Preparation of tert-butyl 8-hydroxy -3,6-dioxaoctanoate

A solution of 53 g of 2-hydroxyethyl ether (0.5 mol) in 200 mL of tetrahydrofuran was prepared, and the solution cooled in an ice-water bath. The solution was placed under a slow stream of argon. Sodium bis(trimethylsilyl)amide (125 mL, 0.125 mol, 1 M in tetrahydrofuran) was added dropwise over a 30 minute period. The mixture was stirred an additional 30 minutes, then 24.4 g of tert-butyl 2-bromoacetate (0.125 mol) was added. The mixture was then stirred for 1 hour. The ice-water bath was removed, and the mixture transferred to a separatory funnel using 250 mL of 1 M $NaH_2PO_4$. The mixture was extracted with ethyl acetate (3×150 mL). The combined extracts were dried over sodium sulfate, filtered, and the solvent removed by rotary evaporator to give a clear yellow liquid. The liquid was purified by chromatography using 500 mL of silica gel and eluting with ethyl acetate/hexanes 1:1. The product was isolated as a clear, gold liquid. Obtained 5.49 g TLC $R_f$ 0.50 (EtOAc). NMR (DMSO-$d_6$)δ 1.42 (s, 9H), 3.42 and 3.54 (m, 8H), 3.98 (s, 2H).

b) preparation of 8-tert-butyloxy-8-oxo-3,6-dioxaoctyl (2-benzoylthioacetyl)glycylglycylglycinate To a solution of 3.69 g of (2-benzoylthioacetyl)-glycylglycylglycine (10 mmol, prepared as above) in 50 mL of dimethylformamide was added 0.12 g of 4-dimethylaminopyridine (1 mmol), 2.05 g of tert-butyl 8-hydroxy-3,6-dioxaoctanoate (10 mmol, prepared as above) and 2.07 g of dicyclohexylcarbodiimide (10 mmol). The initially clear solution developed a precipitate with time. The mixture was stirred at room temperature for 60 hours. The solids were removed by filtration. The solvent was removed from the filtrate by rotary evaporator (vacuum pump, bath temperature 40°) to give the product as a yellow wax. This wax was taken up in 175 mL of boiling 2-propanol, filtered hot, and the solution let cool to room temperature. The product precipitated out as a beige solid. This solid was filtered off and dried under vacuum over $P_2O_5$ to give 2.97 g (52%) TLC $R_f$ 0.31 (chloroform/2-propanol 9:1). NMR (DMSO-$d_6$) δ 1.42 (s, 9H), 3.58 (m, integral obscured by water peak), 3.78 (m, 4H), 3.89 (s,m, 4H), 3.99 (s, 2H), 4.15 (m, 2H) 7.58 (m, 2H), 7.71 (t, 1H), 7.95 (m, 2H), 8.25 (m, 2H), 8.48 (m, 1H).

c) Preparation of 8-succinimidyloxy-3,6-dioxa-8-oxooctyl (2-benzoylthioacetyl)glycylglycylglycinate (Compound III)

A solution of 8-tert-butyloxy-3,6- dioxa-8-oxooctyl (2-benzoylthioacetyl)glycylglycylglycinate (2.71 g, 4.89 mmol, prepared as above) was prepared in 7 mL of trifluoroacetic acid. The clear solution was stirred for 1 hour at room temperature. The trifluoroacetic acid was removed by rotary evaporator (water aspirator, bath temperature 25 ). The residual oil was taken up several times in chloroform and the solvent removed by rotary evaporator. The residue was dried under vacuum overnight to give a yellow solid. NMR spectroscopy confirmed the loss of the tert-butyl ester. The solid was dissolved in 50 mL of dimethylformamide/tetrahydorfuran 1:1. To the solution was added 0.06 g of 4-dimethylaminopyridine (0.49 mmol), 0.56 g of N-hydroxysuccinimide (4.9 mmol) and 2.02 g of dicyclohexylcarbodiimide (9.8 mmol). The solution was stirred for 48 hours at room temperature. An additional 0.5 g of dicyclohexylcarbodiimide was then added, and the mixture stirred an additional 5 hours at room temperature. The resultant solids were filtered off, and the solvents removed from the filtrate by rotary evaporator (water aspirator followed by vacuum pump, bath temperature ≦ 40°) to give the product as an oil. The oil was dried under vacuum overnight to give a brown colored wax. The wax was taken up in 85 mL of hot 2-propanol, filtered while hot and allowed to cool to room temperature. The product precipitated out and was collected by filtration. Drying under vacuum gave 1.0 g of a beige powder (34%). $R_f$ 0.77 (butanol/acetic acid/water 5:2:3). NMR (DMSO$d_6$)δ 2.83 (s, 4H), 3.61 (m, 6H), 3.77 (m, 4H), 3.89 (s +m, 4H) 4.16 (m, 2H), 4.62 (s, 2H), 7.58 (m, 2H), 7.71 (t, 1H), 7.93 (m, 2H), 8.26 (m, 2H), 8.49 (m, 1H).

Example III: Preparation of (2-Thioacetyl)glycylglycylglycylpenta-L-lysine-Fab' Conjugate and Technetium-99m Labeling a) Preparation of the Penta-L-Lysine-Fab' Conjugate

To a solution of 3.06 mg penta-L-lysine (3.03 mmol) in 0.95 mL of 0.10 M phosphate buffer pH 7.00 containing 1 mM EDTA was added 50 μL of a solution of 2.8 mg/0.60 mL of sodium 3-sulfosuccinimidyl 4-N-maleimidomethylcyclohexanecarboxylate in pH 7.00 buffer (0.53 μmol). The solution was mixed, then let stand for 30 minutes at room temperature. The penta-L-lysine solution was added to 0.95 mL of antimyosin Fab' in pH 7.00 buffer (3.11 mg/mL, 3.48 sulfhydryls per mole). The solution was mixed, then let stand for 1 hour at room temperature. The modified Fab' was purified on a MonoS ® cation exchange column (0.5×5 cm), eluting with a linear gradient of 25mM sodium acetate (pH 5.10) and 1.5 M sodium chloride in 25 mM sodium acetate (pH 5.10) over a 20 minute period. Two broad, overlapping peaks were collected at 14 and 17 minutes (ca. 0.6 M NaCl). The purified protein was immediately diluted with an equal volume of pH 7.00 buffer, and concentrated to 2 mg/mL.

b) Preparation of the Benzoylthioacetyltriglycyl-penta-L-lysine-Fab' Conjugate To 0.5 mL of the purified penta-L-lysine-Fab' conjugate (1 mg) was added 30 μL of a solution of succinimidyl benzoylthioacetylglycylglycylglycinate, Compound II, prepared as above (5.8 mg/0.48 mL of DMF, 0.78 mmol). The solution was mixed, then let stand for 1 hour at room temperature. The modified protein was purified by Sephadex G25 M chromatography, eluting with 0.10 M phosphate buffer pH 7.00 containing 1 mM EDTA.

c) Deprotection, Technetium Labeling and Biodistribution

The Sephadex G25 purified benzoylthioacetyltriglycinepenta-L-lysine-Fab' conjugate prepared above was concentrated to 0.60 mL. To this solution was added 0.60 mL of 1 M hydroxylamine in 0.5 M HEPES buffer pH 7.50. The solution was mixed, then let stand for 5 minutes at room temperature. The deprotected conjugate was then purified by Sephadex G25 M chromatography (1×16 cm), eluting with 0.10 M phosphate buffer pH 7.00 containing 1 mM EDTA, taking 1 mL fractions. Aliquots (100 μL) of each fraction were diluted to 1.0 mL with 0.10 M phosphate buffer pH 8.10 containing 1 mM EDTA. For each diluted fraction $A_{280}$ was determined. To each diluted fraction 50 μL of 5.0 mg/mL 5,5'-dithiobis(2-nitrobenzoic acid) in pH 8.10 buffer was added. The samples were mixed, let stand for 15 minutes at room temperature, then $A_{412}$ determined. Protein concentration was determined by $E_{280}$ (1%)=14.0, sulfhydryls per mole was determined by a protein molecular weight of 50,000 and an absorption coefficient of 15,800. Found: 1.02 mg/mL and 2.9 sulfhydryls per mole. To 0.50 mL of 13 mg D-glucaric acid monopotassium salt in 0.10 M phosphate buffer pH 7.50 was added 0.50 mL of sodium [Tc-99m]pertechnetate (Mo-99/Tc-99m generator eluate, 17 mCi) followed by 5 μL of 5.0 mg/mL stannous chloride in 0.2 N HOAc. The solution was mixed, then let stand for 5 minutes at room temperature. An aliquot (0.75 mL) was added to 0.75 mL (0.75 mg) of the deprotected protein conjugate. The solution was mixed, then let stand for 1 hour at room temperature. An aliquot (1.0 mL) of the labeled protein was filtered through a 0.22 μm filter, and the filter washed with 7 mL of saline. The combined washes (8.4 mCi, 8.0 mL, 0.50 mg protein) were used in a biodistribution study. Mice were injected with the labeled protein (0.1 mL), then sacrificed (n=3) at the indicated time points and the organs were counted. The data are given in Table 1. An aliquot (10 μL) of the labeled protein (5 μg) was diluted to 1.0 mL with 1% bovine serum albumin in phosphate buffered saline (BSA/PBS). An aliquot (100 μL) of this dilution was applied to a myosin-Sepharose column. The column was eluted with 10×1.0 mL of 1% bovine serum albumin in phosphate buffered saline (unbound fractions), followed by 10×1.0 mL of 0.10 M glycine buffer, pH 2.53 (bound fractions). The bound and unbound fractions were counted, and immunoreactivity determined. Found: 97% immunoreactive, 93% recovery.

What is claimed is:

1. A protein conjugate comprising:
   a pharmaceutical protein covalently linked to at least one positively charged agent, said protein conjugate having a positive charge in aqueous solution at physiological pH, and said positively charged agent comprising a polymer of three or more subunits selected from the group consisting of amino acids containing positively charged side chains and alkylamines; and
   a radionuclide attached to said pharmaceutical protein or to said positively charged agent through a bifunctional coupling agent which is bound to a site on said protein or on said positively charged agent and to said radionuclide, wherein said bifunctional coupling agent has the formula:

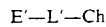

where:
   E' is a moiety bound to a site on said protein or on said positively charged agent;
   Ch is a moiety chelating said radionuclide; and
   L' is a linking radical having the formula:

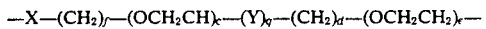

wherein f is an integer from 0 to 6; d and e are independently integers from 0 to 5 inclusive; c is an integer of from 0 to 5 inclusive; q is 0 or 1; X is selected from the group consisting of —NH—, —O— or —S—; Y is selected from the group consisting of —CH$_2$COO—, OOCH$_2$—, —CH$_2$CONH—, OCH$_2$COO—, —NHCOCH$_2$—, and —OOCCH$_2$O—; provided that, when X is other than —O—, then q is 1 and y is other than —CH$_2$CONH— or —NHCOCH$_2$—, and that when f is 0, then c and q are also 0.

2. The protein conjugate of claim 1 where said positively charged agent is selected from the group consisting of polyethyleneimine and polymers or copolymers of one or more amino acids having positively charged side chains selected from the group consisting of alkylamines, alkylamidines, and alkylguanidines, each optionally containing one or more alkyl substituents.

3. The protein conjugate of claim 2 where said positively charged agent is selected from the group consisting of polymers of lysine, ornithine, 2,4-diaminobutyric acid, arginine, and copolymers of said amino acids.

4. The protein conjugate of claim 3 where said polymers or copolymers comprise three to ten repeat units of said amino acids.

5. The protein conjugate of claim 3 where said positively charged agent is an L-lysine polymer.

6. The protein conjugate of claim 5 where said L-lysine polymer comprises four to eight repeat units of L-lysine.

7. The protein conjugate of claim 1 where said protein conjugate comprises a protein in combination with a therapeutic or diagnostic agent.

8. The protein conjugate of claim 7 where said protein comprises an antibody or antibody fragment.

9. The protein conjugate of claim 8 where said protein comprises a Fab' fragment.

10. The protein conjugate of claim 1 where said positively charged agent is covalently linked directly to said protein.

11. The protein conjugate of claim 1 where said positively charged agent is covalently linked to said protein through a bonding radical which is bound to a site on said protein and to a site on said positively charged agent.

12. The protein conjugate of claim 11 where said bonding radical comprises a compound of the formula E—L—A where E is bound to a site on said protein, A is bound to a site on said positively charged agent, and L is an organic linking radical.

13. The protein conjugate of claim 12 where E is a sulfhydryl selective electrophile.

14. The protein conjugate of claim 13 where E is selected from the group consisting of haloalkyl, sulfonate esters, maleimide and aziridine.

15. The protein conjugate of claim 14 where E is selected from the group consisting of ClCH$_2$CONH—, BrCH$_2$CONH—, ICH$_2$CONH— and maleimide.

16. The protein conjugate of claim 12 where A is selected from the group consisting of active esters, imidate esters, epoxides and aldehydes.

17. The protein conjugate of claim 16 where A is an active ester.

18. The protein conjugate of claim 17 where A is an ester of N-hydroxysuccinimide.

19. The protein conjugate of claim 12 where L is selected from the group consisting of optionally substituted alkyl, optionally substituted alkyl containing heteroatom substituents for carbon, and optionally substituted aryl groups.

20. The protein conjugate of claim 12 where L is selected from compounds of the formula —CH$_2$-cyclo-C$_6$H$_{10}$—, —CONHCH$_2$CH$_2$—, —CH$_2$C$_6$H$_4$, —NHCH$_2$CH$_2$— and —OCH$_2$CH$_2$OCH$_2$CH$_2$OCH$_2$CO—.

21. The protein conjugate of claim 11 where said bonding radical is the compound 3-sulfosuccinimidyl 4-(N-maleimidomethyl)cyclohexane-1-carboxylate.

22. The protein conjugate of claim 1 where said positively charged agent is a polymer of L-lysine having from 4 to 8 repeat units of L-lysine; where said positively charged agent is covalently linked to said protein through a bonding radical comprising a compound of the formula E—L—A where E is selected from the group consisting of ClCH$_2$CONH—, BrCH$_2$CONH—, ICH$_2$CONH— and maleimide, A is an ester of N-hydroxysuccinimide, and L is a linking radical.

23. The protein conjugate of claim 22 where said protein is a Fab' fragment.

24. The protein conjugate of claim 1 where E' is a sulfhydryl selective electrophile.

25. The protein conjugate of claim 24 where E' is selected from the group consisting of haloalkyl, sulfonate ester, maleimide and aziridine.

26. The protein conjugate of claim 25 where E' is selected from the group consisting of $ClCH_2CONH-$, $BrCH_2CONH-$, $ICH_2CONH-$ and maleimide.

27. The protein conjugate of claim 1 where E' is selected from the group consisting of active esters, imidate esters, epoxides and aldehydes.

28. The protein conjugate of claim 27 where E' is an active ester.

29. The protein conjugate of claim 28 where E' is an ester of N-hydroxysuccinimide.

30. The protein conjugate of claim 1 where L' contains at least one cleavable site.

31. The protein conjugate of claim 1 where f, d and e are each 2, c and q are each 1, X is —O— and Y is —OCH$_2$COO—.

32. The protein conjugate of claim 1 where Ch is selected from radicals of the formulas:

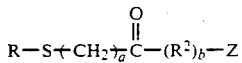

and

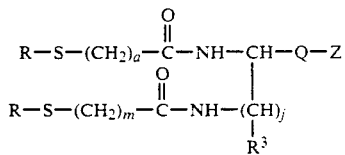

wherein a, j and m are independently an integer of 1 to 3 inclusive; b is an integer from 3 to 6, inclusive; R is selected from the group consisting of $R^1CO—$ or $R^1S—$; $R^1$ is selected from the group consisting of methyl, optionally substituted lower alkyl and optionally substituted aryl; each $R^2$ is independently selected from the group consisting of units

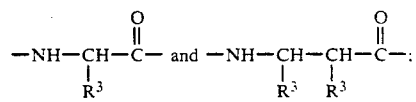

Q is selected from the group consisting of a carbonyl group and $—CHR^3$; each $R^3$ is independently selected from the group consisting of hydrogen, optionally substituted lower alkyl, and optionally substituted aryl; and Z designates the site of attachment of the organic linking radical L'.

33. The protein conjugate of claim 32 where a, j and m are each 1; b is 3, R is $R^1CO—$, $R^1$ is selected from the group consisting of phenyl and phenyl substituted with a functional group; $R^2$ is $NHCH(R^3)CO—$; and $R^3$ is hydrogen.

34. A protein conjugate comprising:
a pharmaceutical protein covalently linked to at least one positively charged agent, said protein conjugate having a positive charge in aqueous solution at physiological pH, and said positively charged agent comprising a polymer of three or more subunits selected from the group consisting of amino acids containing positively charged side chains and alkylamines; and a radionuclide attached to said pharmaceutical protein or to said positively charged agent through a bifunctional coupling agent which is bound to a site on said protein or on said positively charged agent and to said radionuclide, wherein said bifunctional coupling agent has the formula:

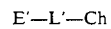

where:

E' is a moiety bound to a site on said protein or on said positively charged agent selected from the group consisting of esters of N-hydroxysuccinimide;

L' is a linking radical having the formula:

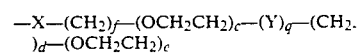

where f, d and e are each 2, c and q are each 1, X is —O— and Y is —OCH$_2$COO—; and Ch is a moiety chelating said radionuclide having one of the formulas:

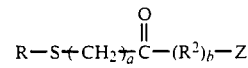

or

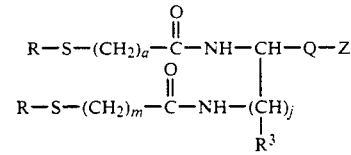

where a, j and m are 1; b is 3; R is $R^1CO—$; $R^1$ is phenyl or phenyl substituted with a functional group; $R^2$ is $NHCH(R^3)CO—$; Q is a carbonyl group or $—CHR^3—$; and $R^3$ is H; and Z designates the site of attachment of the organic linking radical L'.

35. The protein conjugate of claim 34 where said positively charged agent is a polymer of L-lysine having from 4 to 8 repeat units of L-lysine; where said positively charged agent is covalently linked to said protein through a bonding radical comprising a compound of the formula E—L—A where E is selected from the group consisting of $ClCH_2CONH—$, $BrCH_2CONH—$, $ICH_2CONH—$ and maleimide, A is an ester of N-hydroxysuccinimide and L is a linking radical.

36. A protein conjugate comprising:
a pharmaceutical protein covalently linked to at least one positively charged agent, said protein conjugate having a positive charge in aqueous solution at physiological pH, and said positively charged agent comprising a polymer of three or more subunits selected from the group consisting of amino acids containing positively charged side chains and alkylamines; and a radionuclide attached to said pharmaceutical protein or to said positively charged agent through a bifunctional coupling agent which is bound to a site on said protein or on said positively charged agent and to said radionuclide, wherein said bifunctional coupling agent has one of the following formulas:

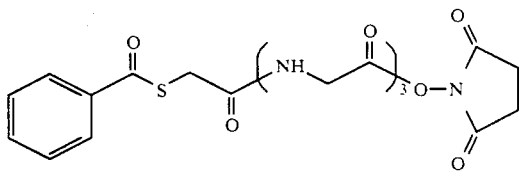

or

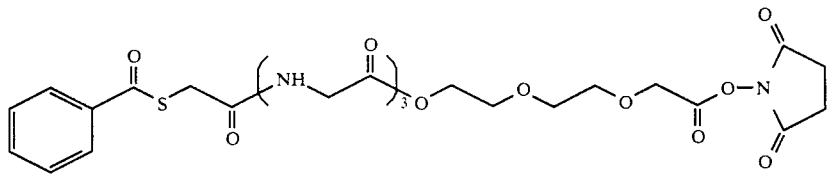

37. A method of preparing the protein conjugate of claim 10 comprising contacting a protein with an excess of said positively charged agent and a limiting amount of a water soluble carbodiimide.

38. A method of preparing the protein conjugate of claim 11 comprising:
   (A) contacting said positively charged agent and said bonding radical under conditions effective to bond said agent and said radical; and
   (B) contacting the product of step (A) with said protein.

39. A radiodiagnositc or radiotherapeutic precursor comprising:
   A protein covalently linked to at least one positively charged agent, said protein conjugate having a positive charge in aqueous solution at physiological pH, and said positively charged agent comprising a polymer of three or more subunits selected from the group consisting of amino acids containing positively charged side chains and alkylamines; and
   at least one bifunctional coupling agent bound to said protein or to said positively charged agent, wherein said bifunctional coupling agent has the formula:

E'—L'—Ch where E', Ch and L' have the meaning set forth at claim 1.

40. The radiodiagnositc or radiotherapeutic precursor of claim 39 where said at least one bifunctional coupling agent is bound to said positively charged agent.

41. The radiodiagnostic or radiotherapeutic precursor of claim 40 where a plurality of bifunctional coupling agents are bound to said positively charged agent.

42. A radiodiagnostic or radiotherapeutic agent comprising the radiodiagnostic or radiotherapeutic precursor of claim 39 and a metallic radionuclide bound to at least one bifunctional coupling agent of said precursor.

43. A radiodiagnostic or radiotherapeutic agent comprising the radiodiagnostic or radiotherapeutic precursor of claim 40 and a metallic radionuclide bound to at least one bifunctional coupling agent of said precursor.

44. A radiodiagnostic or radiotherapeutic agent comprising the radiodiagnostic or radiotherapeutic precursor of claim 41 and a metallic or nonmetallic radionuclide bound to at least one bifunctional coupling agent of said precursor.

45. A radiodiagnostic or radiotherapeutic agent of claim 42 where said metallic radionuclide is selected from the group consisting of Tc, In, Re, Ga, I and Y.

46. A kit for use with a metallic or nonmetallic radionuclide for preparing a radiodiagnostic or radiotherapeutic agent comprising a radiodiagnostic or radiotherapeutic precursor of claim 40.

* * * * *

UNITED STATES PATENT AND TRADEMARK OFFICE
CERTIFICATE OF CORRECTION

PATENT NO. : 5,162,505
DATED : November 10, 1992
INVENTOR(S) : Dean et al.

It is certified that error appears in the above-identified patent and that said Letters Patent is hereby corrected as shown below:

Column 1, Line 51 delete "Krejcare" and insert therefor --Krajcarek--.

Column 2, Line 34 delete "Ned.," and insert therefor --Med.,--.

Column 4, Lines 64-65, delete "active ester"" and insert therefor --"active ester"--.

Column 5, Line 17 delete "N-substituted"

Column 12, Line 21 delete "obtained" and insert therefor --Obtained--.

Column 12, Line 34 delete "35." and insert therefor --35°--.

Column 13, Line 39 delete "25 )." and insert therefor --25°).--.

Column 13, Lines 15-16 delete "/tetrahydorfuran" and insert therefor --/tetrahydrofuran--.

Signed and Sealed this

Twenty-third Day of November, 1993

Attest:

BRUCE LEHMAN

Attesting Officer

Commissioner of Patents and Trademarks